United States Patent [19]
Royal

[11] Patent Number: 4,832,949
[45] Date of Patent: May 23, 1989

[54] DEPILATORY COMPOSITION

[76] Inventor: Carola C. Royal, 12266 E. Ohio Ave., Aurora, Colo. 80012

[21] Appl. No.: 63,325

[22] Filed: Jun. 18, 1987

[51] Int. Cl.$^4$ ............................................. A61K 7/155
[52] U.S. Cl. ........................................ 424/73; 8/160; 8/161
[58] Field of Search .................. 424/73; 8/94.16, 160, 8/161

[56] References Cited

U.S. PATENT DOCUMENTS 2,091,313  8/1937  Grant ...................................... 8/160

FOREIGN PATENT DOCUMENTS 2267755  12/1975  France ..................................... 8/161
901624   7/1962  United Kingdom ..................... 8/160
1242083  8/1971  United Kingdom .
2157951  11/1985  United Kingdom .

OTHER PUBLICATIONS

Computer Printout showing Brazilian Patent Application No. 02183-A, published 12-16-86 to N. J. S. Correa.

Primary Examiner—Ellis P. Robinson
Assistant Examiner—Susan S. Rucker
Attorney, Agent, or Firm—John E. Reilly

[57] ABSTRACT

A depliatory composition for removal of hair from the human skin is made up of a mixture of honey, sugar and citric acid which mixture is heated to a predetermined temperature level, then allowed to cool so as to form a highly viscous, wax-like composition which can be applied manually in slender strips to the skin. The composition will firmly adhere to the hair with which it comes into contact and, by quickly drawing away from the skin, will cause the hair to be removed from its root but without causing undue irritation and swelling.

8 Claims, No Drawings

DEPILATORY COMPOSITION

This invention relates to depilatories; and more particularly relates to a novel and improved depilatory composition of a wax-like consistency which is specifically adaptable for use in removing hair from the human body, such as, for example, eyebrows and other facial hair, legs or arms.

BACKGROUND AND FIELD OF THE INVENTION

The removal of hair from the human body has received considerable attention. The hair and hair follicles can be removed by certain surgical operations or by electrolysis. Also it is customary to remove hair by the use of tweezers or other instruments but does not have the same long lasting effects as surgical procedures. Moreover, the use of hair removal instruments is generally confined to removal of hair from a localized area, such as, along the eyebrows or nostrils.

Creams or cold waxes have been formulated in the past for the purpose of hair removal to the end of achieving more lasting effects as well as the ability to apply over greater areas than is possible by plucking out individual hairs from a localized part of the body. For example, it has been proposed in the past to employ a combination of honey, rosin and wax which are heated together and thereafter combined with citric acid which is mixed into the composition until it has acquired a creamy texture, reference being made to U.S. Pat. No. 2,091,313 to W. M. Grant. Grant fails to state to what temperature level the formulation is heated. Moreover, the use of a wax composition, such as, beeswax has been found to irritate the skin and to cause redness and swelling.

British Letters Pat. No. 901,624 to E. Wenden discloses the formulation of a cream made up of sugar and lemon juice, glycerine, boric acid powder, sodium chloride and a water carrier. These ingredients are heated, then allowed to cool to a temperature at which they may be poured into separate jars or containers, and specifically are heated to a temperature on the order of 278° F. to form a plastic mass. The resultant composition is applied to the skin so as to become matted with the hair, then immediately stripped from the skin to cause removal of the hair with the plastic mass.

Another British Letters Pat. No. 1,242,083 to M. Doughty also discloses the combination of sugar with citric acid and water in the formation of a depilatory or hair removal composition. Generally, the approach taken in Doughty is to boil the mixture for a short period or optionally to simmer over longer periods but makes no distinction as to the relative effect of boiling versus simmering. Once again the resultant composition is alleged to be of the consistency of paste and which will not harden when applied to the skin and, being water soluble, can be readily cleaned off of the skin; and Doughty proposes the optional addition either of a gelatin or isinglass. It has been found that the use of gelatin tends to leave a burning sensation when applied to the skin as well as to cause swelling and discoloration. Moreover the composition of sugar and gelatin as disclosed by Doughty would not appear to possess the capability of removing dead skin cells or of exfoliating the skin so as to leave a natural glow when the process is completed.

In the formulation of a depilatory composition, it is highly desirable that the composition be composed entirely of natural ingredients, can be readily applied with a finger or fingers over a closely controlled area without adhering to the fingers so as to uniformly and firmly adhere to the hair, and can be readily removed by grasping and pulling quickly away from the skin to effect the complete removal of hair over the applied area without necessity of repeating the process. Further, in this connection, it is most desirable that the composition will not cause swelling or other irritation to the skin.

SUMMARY OF THE INVENTION

It is therefore an object of the present invention to provide for a novel and improved depilatory composition for the effective removal of hair from the skin.

Another object of the present invention is to provide for a hair removal composition adaptable for use in removing hair from parts of the human body and is composed entirely of natural ingredients, can be quickly and easily formulated and produced and possesses good shelf life.

A further object of the present invention is to provide for a novel and improved depilatory composition and method of preparing same which can be applied to closely controlled areas of the human body for the purpose of complete and efficient hair removal from those areas without causing irritation or swelling, is water-soluble and does not cause any substantial discoloration of the skin.

A still further object of the present invention is to provide for a novel and improved depilatory composition which when applied in thin strips is capable of removing dead skin cells along with hair from the human skin, does not require repeated applications to the same area in order to effect complete removal of the hair down to the roots and is longlasting.

In accordance with the present invention, there has been devised a novel and improved depilatory composition which is of a wax-like consistency and can be applied over selected areas of the skin to effect complete hair removal therefrom. In the preferred composition of the present invention, major proportions of honey and sugar are combined together with a minor proportion of citric acid, the honey being present in a greater amount than the sugar, and the ingredients are stirred together over medium heat. The composition is cooked for a time period of 1 to 2 hours, depending upon quantities, until the temperature reaches 275° F. at an altitude of one mile above sea level, but broadly at a temperature level just below that which would cause hardening of the composition. After the cooking operation, the composition is permitted to cool to room temperature and then poured into individual containers. The resultant product will harden somewhat after complete cooling but nevertheless retains its wax-like, pliable consistency.

In applying the depilatory composition to the skin after it has cooled or been stored over extended time periods, it is heated either by warming on the stove or in a microwave until soft enough to permit its removal from the container with the fingers. It is desirable to add a few drops of warm water to the composition as it is removed from the container and to pull and stretch the product with the hands until soft enough to apply to the skin with one hand or one or more fingers of the hand. The product is pressed onto the skin by hand in areas where the hair is to be removed and is worked into the hair so as to assure good adherence to the hair and to the skin over the affected area. Once applied in the manner described, the composition is then quickly stripped or pulled away from the skin with the fingers to effect complete hair removal.

The above and other objects, advantages and features of the present invention will become more readily appreciated and understood from a consideration of the following detailed description of preferred and alternate forms of compositions and procedures for preparing same.

DETAILED DESCRIPTION OF THE PREFERRED EMBODIMENT

In the preparation of the preferred composition of the present invention, a batch of honey and sugar were combined with a limited quantity of lemon juice in a large vat. Preferably, 60% to 65% by weight of honey were combined with 30% to 35% by weight of sugar and 2% to 5% by weight of lemon juice. The honey employed is a pure grade of honey and the sugar is a fine granulated sugar, commonly referred to as sucrose. Powdered sugar has not been found to be as effective in the formulation of the compound as granulated sugar. The ingredients were stirred thoroughly over medium heat and allowed to cook for 1.5 hours to 2 hours to a temperature on the order of 275° F. at one mile above sea level. The preferred method of preparation was carried out at one mile above sea level and appropriate conversion must be made, in accordance with well-known practice, in preparing at sea level or at other altitudes. Generally, the boiling point of any liquid is lower as the altitude increases, and the requisite cooking time is proportionally lengthened as the altitude increases.

The resultant mixture was found to be homogenous and easily pourable when allowed to cool for 5 to 10 minutes. At that point, the mixture was removed from the vat into plastic containers or jars. Upon further cooling to room temperature in the individual jars, the product was found to harden slightly but nevertheless was readily pliable and easy to work. In that condition, the product when stored in individual closed containers has been found to have excellent shelf life and can be stored for an indefinite period of time preliminary to use. In accordance with well-known practice, the citric acid or lemon juice acts as a preservative and minimizes any tendency of the sugar to crystallize when stored over long periods of time.

As a preliminary to applying the product to the skin, most desirably it is heated in a microwave oven on the order of 1 to 2 minutes or can be heated on top of a stove in hot water for longer time intervals until soft enough to be able to scoop out of the jar. Typically the product is best removed from the jar by scooping out with the fingers. A few drops of water may be placed on the hands as a preliminary to removing the product so as to avoid any tendency of the product to stick to the hands and to make it more pliable. The portion removed should be pulled and stretched or kneaded by hand until soft enough to readily apply to the skin with the fingers. For the purpose of applying, a small quantity is placed on the index and middle fingertips of one hand and then pressed into the skin along that section where the hair is to be removed. Extreme pressure is not required although it may be desirable to go over the same area two to three times to assure uniform adherence of the wax along the strip from which the hair is to be removed. In this relation, it is advisable to apply but a limited quantity to an area on the order of 0.5" to 1" wide and 2" to 3" in length. Immediately following application to the skin, the strip of material is then quickly pulled off by hand much in the manner of removing a bandaid from the skin. The application procedure is then repeated as described over or along adjacent strips where the hair is to be removed. Once removed, a wet cold towel or washcloth may be applied to the effected area to close the pores and to soothe the skin. Very little pain is experienced in the process of hair removal with no resultant swelling or irritation beyond that which would be normally experienced in plucking individual hairs from the skin. Any redness or discoloration caused by removal of the hair as found to disappear within twenty-four hours.

The composition may be mixed and prepared in any desired quantities. Of particular importance is the heating procedure to insure that the ingredients are heated to a temperature just below that at which the material will tend to harden. At an altitude one mile above sea level, it was found that the optimum temperature was 275° F. and the optimum cooking period on the order of 1.5 to 2 hours. When cooked to any appreciable extent below the hardening temperature, it was found that the consistency and homogeniety of the mixture were not as good. Even more critical, when boiled or cooked above or to the hardening point, the resultant mixture was virtually impossible to work even to the extent of removing it from the cooking vat.

In the Examples which follow, the method of preparing the composition is exemplified. These Examples illustrate the quantity of ingredients and define the time period for cooking of same.

EXAMPLE I

½ cup of honey: (4 oz.)
1 cup of sugar: (8 oz.)
¼ cup of lemon juice: (2 oz.)

The ingredients were cooked on low heat up to a temperature of 245° F. for a period of 1.5 hours. The resultant product was extremely soft and difficult to apply to the skin.

EXAMPLE II

¾ cup of honey: (6 oz.)
1 cup of sugar: (8 oz.)
¼ cup of lemon juice: (2 oz.)

The ingredients were cooked on low to medium heat up to a temperature of 250° F. for a period of approximately 1.5 hours. Again, the product was difficult to apply to the skin and separated when water was added.

EXAMPLE III

1½ cups of honey: (12 oz.)
¾ cup of sugar: (6 oz.)
2 tablespoons of lemon juice: (2 oz.)

The ingredients were cooked on medium heat up to a temperature of 255° F., but found to be too soft to apply to the skin after a period of 1.5 hours cooking.

EXAMPLE IV 1 cup of honey: (8 oz.)
2 cups of sugar: (16 oz.)
¼ cup of lemon juice: (2 oz.)

The ingredients were cooked on medium heat up to a temperature of 260° F. for a period of 1.5 hours. The resultant material was very grainy and did not feel comfortable when applied to the skin and not sufficiently viscous.

EXAMPLE V 1 cup of sugar: (8 oz.)
1 cup of honey: (12 oz.)
½ cup of lemon juice: (4 oz.)
2 tablespoons of baking soda: (2 oz.)

When cooked on medium heat up to a temperature of 260° F. for a period of 1 hour, the product was found to be too sticky and difficult to apply to the skin.

EXAMPLE VI

¾ cup of honey: (9 oz.)
1 cup of sugar: (8 oz.)
¼ pound of honey comb
3 tablespoons of lemon juice: (3 oz.)

The materials were cooked on medium heat up to a temperature of 270° F. for a period of 1 hour but again the resultant product was found to be difficult to apply to the skin.

EXAMPLE VII

¾ cup of honey: (9 oz.)
¾ cup of sugar: (6 oz.)
¼ cup of lemon juice: (2 oz.)
¼ of beeswax: (3 oz.)

The materials were stirred together and cooked on medium heat up to a temperature of 275° F. for a period of 1 hour. The resultant product could be more easily applied to the skin but it was found that the beeswax irritated the skin.

EXAMPLE VIII 1 cup of sugar: (8 oz.)
¾ cup of honey: (9 oz.)
2 tablespoons of lemon juice: (2 oz.)

The ingredients were mixed as described and cooked on high heat at 300° F. but would not apply satisfactorily to the skin; and was very much like a hard candy after a period of cooking for 1 hour.

EXAMPLE IX 1 cup of sugar: (8 oz.)
1 cup of honey: (12 oz.)
2 tablespoons of lemon juice: (2 oz.)

The ingredients were cooked at 280° F. on high heat for 1 hour but found to be too hard to apply to the skin.

EXAMPLE X 1 cup of honey: (12 oz.)
¾ cup of sugar: (6 oz.)
2 tablespoons of lemon juice: (2 oz.)

The ingredients were stirred and cooked at 275° F. on medium heat for 1 hour. The resultant product was found to be easy to apply to the skin but with sufficient adherence to effectively remove the hair when lifted from the skin.

With respect to all of the working Examples described, the wax product once cooked was allowed to cool for a period of 5 to 10 minutes, then poured into plastic jars. The product was permitted to harden which in the case of the preferred wax formula as described in Example X required a period of 2 hours before it hardened to the desired consistency. In the working Examples given, the relative proportions by volume and weight as given are approximate and may vary ± one-half ounce.

Generally, in applying to the skin for the purpose of hair removal, the skin should be dry and free of oils and creams. The composition, once prepared as described, should be softened by immersing the jar in gently boiling water for a period of 20 to 30 minutes; or if desired it may be heated in a microwave oven for a short period of time on the order of 1 to 2 minutes depending upon the power rating of the oven. When heated in boiling water, the product should be tightly covered so as to avoid exposure to water or steam. Once the product has softened, the fingertips should be wetted and the desired amount of the product to be applied should be removed from the container with the fingertips and the product pulled and stretched until pliable. Holding the index and middle fingers together, the wax is spread in strips on the skin by pressing down firmly, going over the same section two to three times if desired. The strip of material is then pulled off quickly by lifting much in the manner or approach used to remove a bandaid.

If the product hardens while using, drops of warm water may be added and the product pulled and stretched until the water is absorbed. After applying the wax over a desired area and removing as described, a cold wet towel or washcloth is applied to the treated area for a limited period of time to close the pores and to soothe the skin, after which a skin lotion may be applied if desired.

It has been found that in actual use in treating patients for hair removal the preferred substance can be quickly and easily applied in thin strips over closely controlled areas and is sufficiently viscous as not to tend to overrun or spread beyond the strip as applied. This is important, for example, in removal of facial hair, such as, along the eyebrow region so as to leave a well-defined line of demarcation between the eyebrow and adjacent area from which the hair has been removed. Nevertheless, the substance when handled as described is pliable and exhibits excellent adherence qualities when applied in strip form so as to assure complete removal of the hair from its roots without repeated applications. The formulation is composed entirely of natural ingredients and has demonstrated long-lasting effects in hair removal so that the process need not be repeated for weeks at a time. Of course, various carriers to lend desired aromas or fragrances to the wax formulation may be added to the compound but it is believed important to use natural ingredients in the treatment of the skin.

The working Examples demonstrate that the product is most effective when a major proportion of honey is used to that of sugar whether measured in terms of parts by volume or by weight. Thus, as demonstrated in Examples V, VI and VII, equal parts by volume of honey and sugar resulted in a product that was quite sticky and difficult to apply to the skin. Most critical, however, is to maintain the temperature level at 275° F. (one mile above sea level) to avoid undue hardening of the product. Moreover, it is has been found that cooking the composition in a microwave oven at corresponding temperatures nevertheless does not lend satisfactory results in the completed product. Tests made in microwave cooking of the preferred composition at temperatures in the range of 225° F. to 260° F. resulted in a product that was very soft and difficult to control when applied to the skin. On the other hand, in cooking above a temperature of 275° F. the product was found to harden.

It is therefore to be understood that various modifications and changes may be made in the specific composition, method of preparing and applying same without departing from the spirit and scope of the present invention as defined by the appended claims.

I claim:

1. A depilatory composition for the removal of hair from the human skin wherein the composition is to be applied to a portion of the human skin from which the hair is to be removed, said composition comprising major proportions by weight of honey and sugar, and a minor proportion by weight of citric acid, the honey being present in a greater proportion by weight than the combined proportions by weight of sugar and citric acid, said honey, sugar and citric acid being intermixed and heated to a temperature just below the hardening point of the composition so as to be of a wax-like consistency as a preliminary to application to the human skin.

2. A depilatory composition according to claim 1, said honey and sugar being present in the approximate ratio of two parts by weight of honey for each part by weight of sugar.

3. A depilatory composition according to claim 1, said citric acid being lemon juice.

4. The method of preparing a composition for the removal of hair from human skin and of applying the composition to a portion of the human skin from which the hair is to be removed comprising the steps of:

intermixing major proportions of honey and sugar with a minor proportion of citric acid, the proportion of honey being greater than the combined proportion of sugar and citric acid;

cooking said honey, sugar and citric acid to a temperature level on the order of 275° F. at one mile above sea level just below the hardening point of the mixture and continuing to cook the composition at that temperature level without hardening of the composition;

cooling the mixture to room temperature level;

mechanically working the mixture once cooled as a preliminary to application to the skin; and manually applying the mixture in thin strips to the human skin after the mechanical working step, followed by removing each strip so applied immediately after application to the skin.

5. The method according to claim 4, there being a major proportion of not less than 60% by weight of honey, and a minor proportion of not more than 40% by weight of sugar.

6. The method according to claim 4, including the step of adding water to the mixture after the cooling step and preliminary to the mechanical working step.

7. The method according to claim 6, in which the mechanical working step is characterized by manually stretching or kneading the mixture between the hands.

8. The method according to claim 4, further characterized by heating the mixture during the cooking step to a temperature on the order of 275° F. at one mile above sea level.

* * * * *